United States Patent
Roy

(10) Patent No.: US 10,015,567 B2
(45) Date of Patent: Jul. 3, 2018

(54) MOBILE HEALTH SYSTEM

(71) Applicant: Michel Y. Roy, Chicago, IL (US)

(72) Inventor: Michel Y. Roy, Chicago, IL (US)

( * ) Notice: Subject to any disclaimer, the term of this patent is extended or adjusted under 35 U.S.C. 154(b) by 0 days.

(21) Appl. No.: 15/077,561

(22) Filed: Mar. 22, 2016

(65) Prior Publication Data

US 2017/0280209 A1    Sep. 28, 2017

(51) Int. Cl.
*H04Q 9/00* (2006.01)
*A61B 5/00* (2006.01)
*G16H 40/63* (2018.01)

(52) U.S. Cl.
CPC .............. *H04Q 9/00* (2013.01); *A61B 5/00* (2013.01); *G16H 40/63* (2018.01); *H04Q 2209/40* (2013.01)

(58) Field of Classification Search
CPC .. H04Q 9/00; H04Q 2209/40; H04Q 2209/60; G06F 19/3406; G06F 21/32; G06F 21/35; A61B 5/14532; A61B 5/6898; H04B 1/385
See application file for complete search history.

(56) References Cited

U.S. PATENT DOCUMENTS

| | | | |
|---|---|---|---|
| 8,459,559 B2 | 6/2013 | Shadwell, Jr. et al. | |
| D711,860 S | 8/2014 | Daniel | |
| 2008/0208016 A1* | 8/2008 | Hughes | A61B 5/0533 600/301 |
| 2011/0105177 A1 | 5/2011 | Batiz | |
| 2013/0012796 A1 | 1/2013 | Kak et al. | |
| 2013/0076533 A1 | 3/2013 | Moran | |
| 2014/0106676 A1 | 4/2014 | Yarger et al. | |
| 2015/0201884 A1* | 7/2015 | Ashokan | A61B 5/4872 702/19 |
| 2015/0278498 A1* | 10/2015 | Hong | G06F 21/32 340/5.82 |
| 2015/0347711 A1* | 12/2015 | Soli | H04W 4/22 705/3 |
| 2015/0348389 A1* | 12/2015 | Jang | H04W 4/22 455/404.1 |
| 2015/0350861 A1* | 12/2015 | Soli | H04W 4/22 455/404.1 |
| 2016/0070304 A1* | 3/2016 | Shin | H04M 1/0268 361/679.26 |
| 2016/0354042 A1* | 12/2016 | Shim | G06F 21/32 |

* cited by examiner

*Primary Examiner* — Orlando Bousono

(57) ABSTRACT

A mobile health system includes a communication network. An electronic device is provided and the electronic device in electrical communication with the communication network. A sensing unit is removably coupled to the electronic device such that the sensing unit is in electrical communication with the electronic device. The sensing unit may be touched by a user thereby facilitating the sensing unit to record a biometric signal generated by the user. The sensing unit communicates the biometric signal to the electronic device. The electronic device transmits the biometric signal to the communication network. The communication network may communicate the biometric signal to a medical professional. Thus, the medical professional may recommend a medical treatment corresponding to the biometric signal.

6 Claims, 4 Drawing Sheets

MOBILE HEALTH SYSTEM

BACKGROUND OF THE DISCLOSURE

Field of the Disclosure

The disclosure relates to diagnostic devices and more particularly pertains to a new diagnostic device for facilitating frequency based medical treatment to be remotely administered.

SUMMARY OF THE DISCLOSURE

An embodiment of the disclosure meets the needs presented above by generally comprising a communication network. An electronic device is provided and the electronic device in electrical communication with the communication network. a sensing unit is removably coupled to the electronic device such that the sensing unit is in electrical communication with the electronic device. The sensing unit may be touched by a user thereby facilitating the sensing unit to record a biometric signal generated by the user. The sensing unit communicates the biometric signal to the electronic device. The electronic device transmits the biometric signal to the communication network. The communication network may communicate the biometric signal to a medical professional. Thus, the medical professional may recommend a medical treatment corresponding to the biometric signal.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
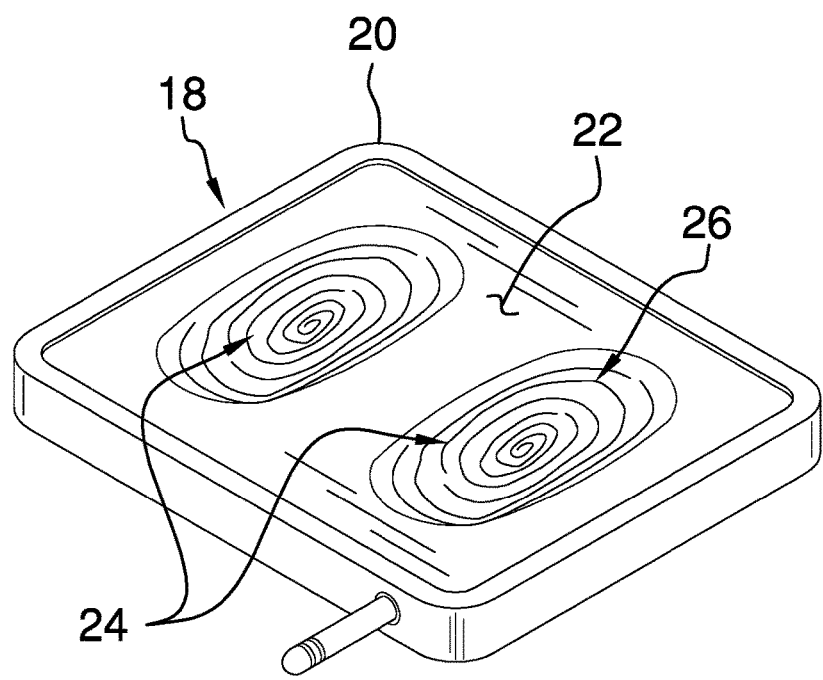
FIG. 1 is a perspective view of a mobile health system according to an embodiment of the disclosure.
Figure 2:
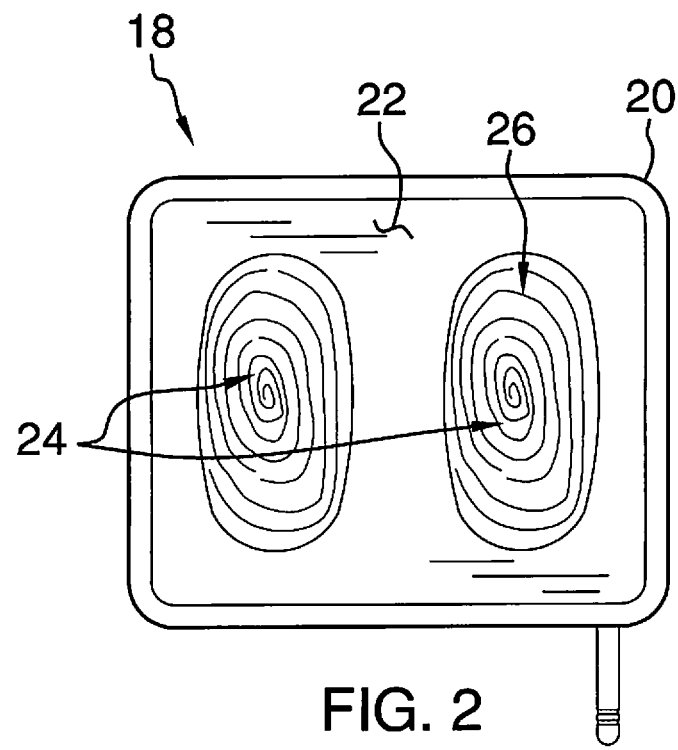
FIG. 2 is a front view of an embodiment of the disclosure.
Figure 3:
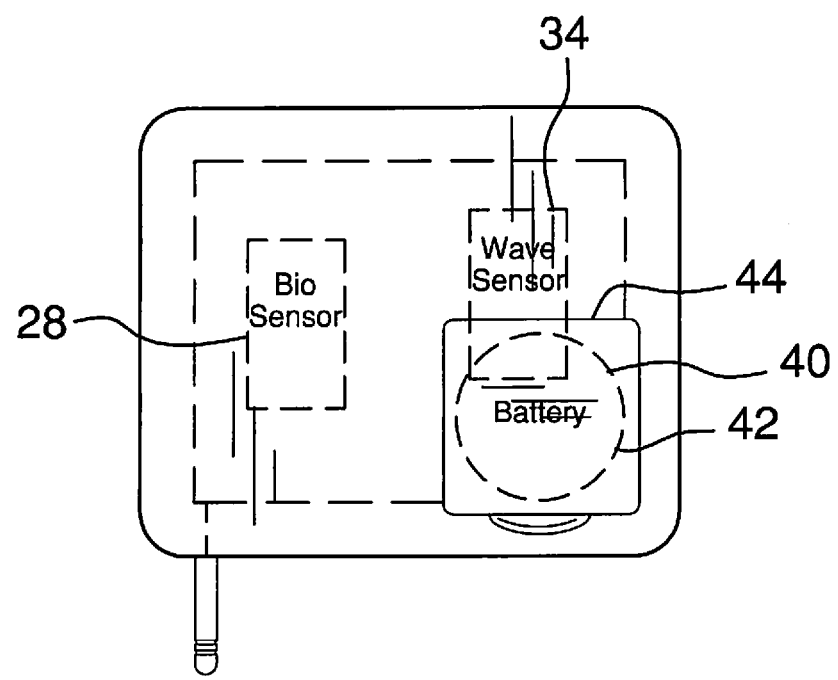
FIG. 3 is a back view of an embodiment of the disclosure.
Figure 4:
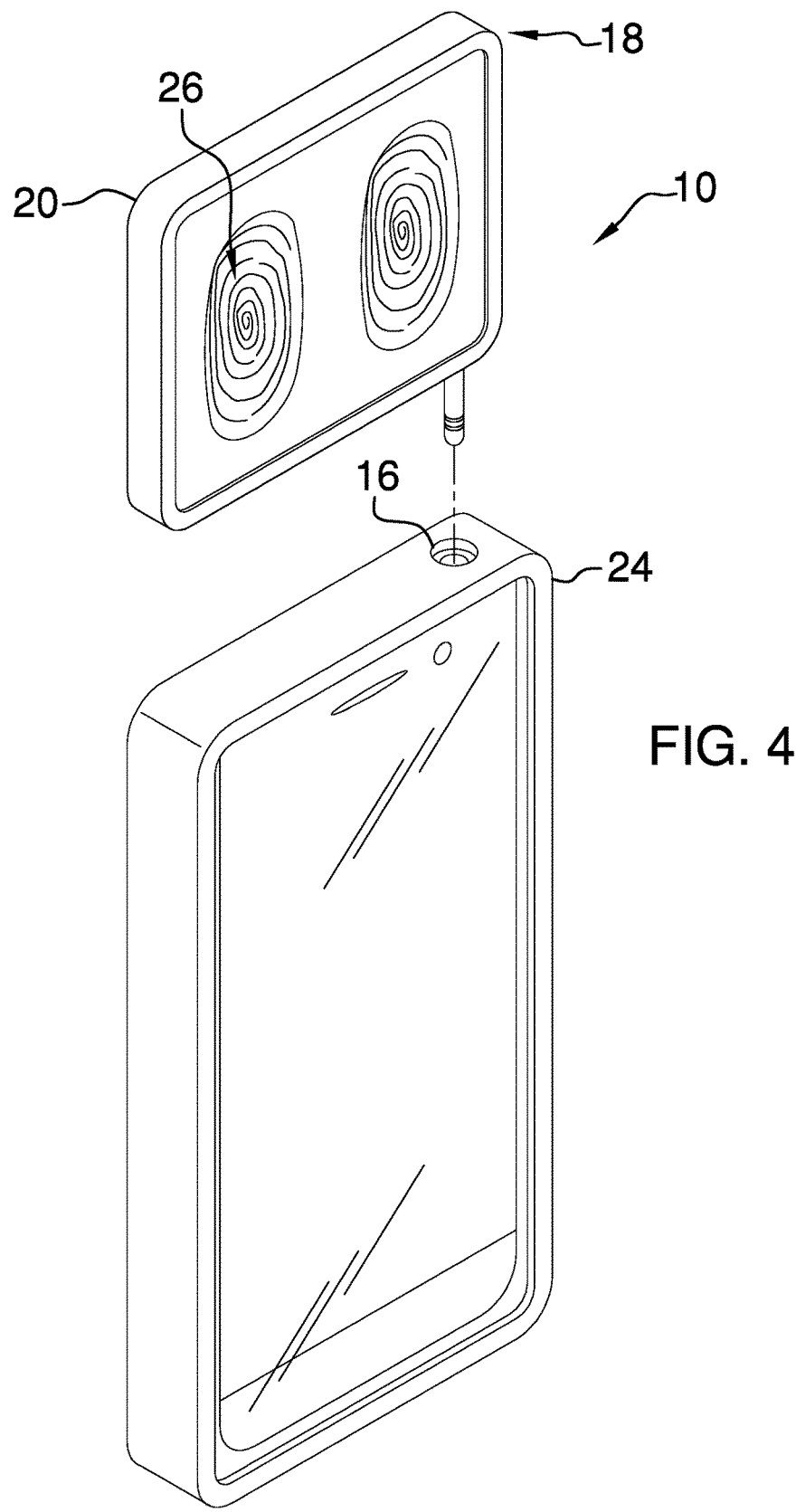
FIG. 4 is a front perspective view of an embodiment of the disclosure.
Figure 5:
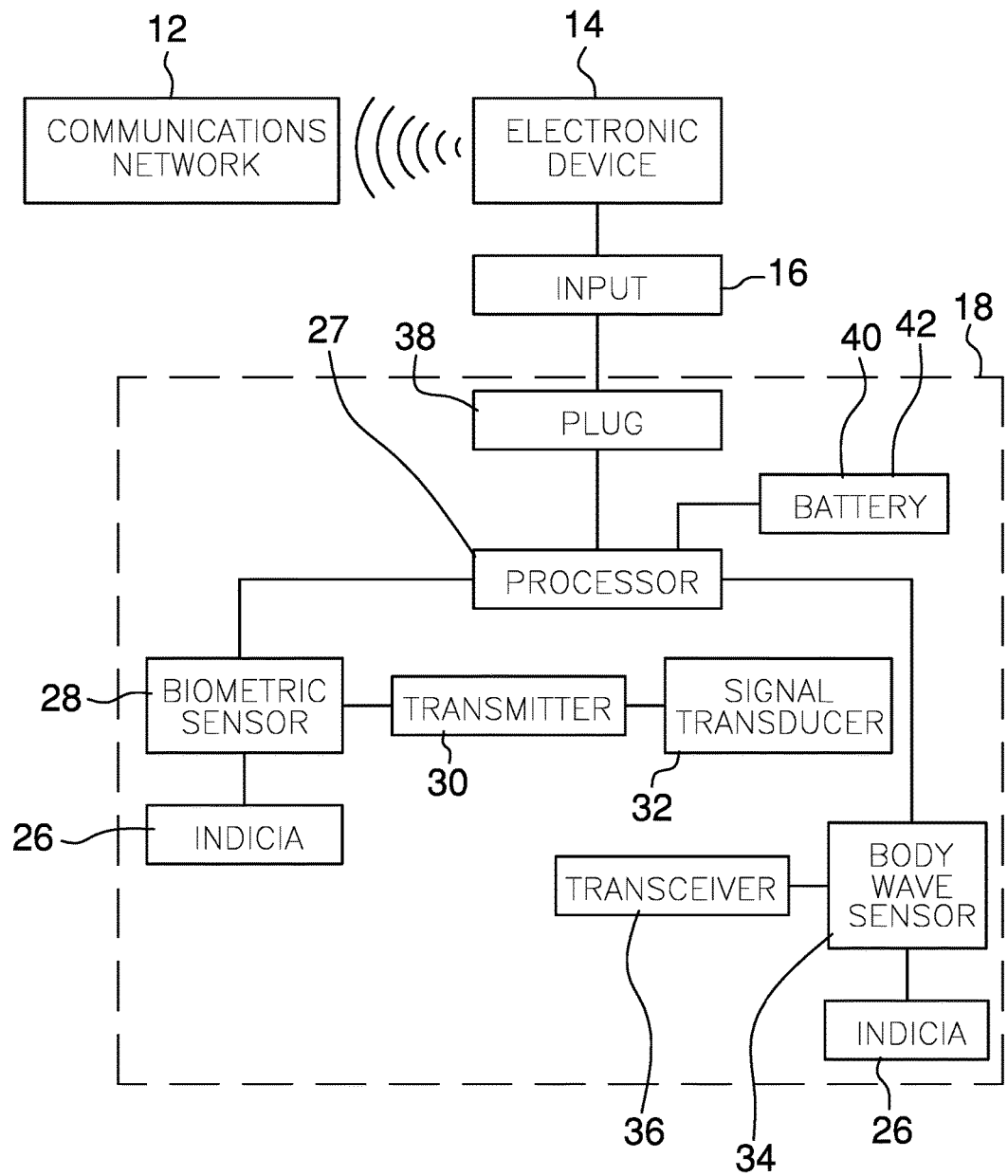
FIG. 5 is a schematic view of an embodiment of the disclosure.

With reference now to the drawings, and in particular to FIGS. 1 through 5 thereof, a new diagnostic device embodying the principles and concepts of an embodiment of the disclosure and generally designated by the reference numeral 10 will be described.

As best illustrated in FIGS. 1 through 5, the mobile health system 10 generally comprises a communication network 12. The communication network 12 may comprise the internet, a mobile phone communication network or the like. Additionally, the communication network 12 may be a global communication network. An electronic device 14 is provided and the electronic device 14 is in wireless electrical communication with the communication network 12. The electronic device 14 has an input 16 and the electronic device 14 may comprise a smart phone or the like.

A sensing unit 18 is removably coupled to the electronic device 14 such that the sensing unit 18 is in electrical communication with the electronic device 14. The sensing unit 18 may be touched by a user thereby facilitating the sensing unit 18 to record a biometric signal generated by the user. The sensing unit 18 communicates the biometric signal to the electronic device 14. The electronic device 14 transmits the biometric signal to the communication network 12. The communication network 12 may communicate the biometric signal to a medical professional or a database. Thus, the medical professional may recommend a medical treatment corresponding to the biometric signal.

The sensing unit 18 comprises a housing 20 that has a front surface 22. The front surface 22 has a pair of depressions 24 and each of the depressions 24 may be touched by the user. The front surface 22 corresponding to each of the depressions 24 may have indicia 26 being printed thereon. The indicia 26 may comprise an image of a fingerprint. Each of the depressions 24 is comprised of an electrically conductive material. Thus, each of the depressions 24 is in electrical communication with the user when the user touches the depressions 24.

A processor 27 is positioned within the housing 20. The processor 27 may comprise an electronic processor or the like. A biometric sensor 28 is positioned within the housing 26 and the biometric sensor 28 is electrically coupled to the processor 27. The biometric sensor 28 is electrically coupled to one of the depressions 24. Thus, the biometric sensor 28 may receive the biometric signal from the user.

The biometric sensor 28 may monitor physiological properties of the user ranging from pulse rate, temperature, blood chemistry and other physical conditions of the user. Additionally, the biometric sensor 28 may monitor coherent and incoherent wave conditions of the user. The biometric sensor 28 may include a transmitter 30 and a signal transducer 32. The transmitter 30 may comprise a radio frequency transmitter or the like. The signal transducer 32 may facilitate the biometric sensor 28 to convert a signal received from the user into an electromagnetic signal. Thus, the electromagnetic signal may be communicated to the communication network 12.

A body wave sensor 34 is positioned within the housing 20. The body wave sensor 34 is electrically coupled to the processor 27. The body wave sensor 34 is electrically coupled to one of the depressions 24. Thus, the body wave sensor 34 may receive an electromagnetic frequency from the user. The body wave sensor 34 may include a transceiver 36. The transceiver 36 may be a radio frequency transceiver or the like. The transceiver 36 may have an operational frequency ranging between 0.0001 Hz and 10,000 Hz. Thus, the body wave sensor 34 may detect electromagnetic frequencies associated with physiological processes occurring within the user.

A plug 38 is coupled to the housing 20 and the plug 38 is electrically coupled to the processor 27. The plug 38 is selectively electrically coupled to the input 16 on the electronic device 14. Thus, the plug 38 may communicate the biometric signal and the electromagnetic frequency to the electronic device 14. The plug 38 may comprise a ¼ inch headphone jack or the like.

A power supply 40 is positioned within the housing 20. The power supply 40 is electrically coupled to the processor 27. The power supply 40 comprises at least one battery 42. A battery cover 44 may be removably coupled to the housing 20. The power supply 40 may be positioned beneath the battery cover 44.

In use, the electronic device 14 communicates the biometric signal and the electromagnetic frequency to the communication network 12. Thus, the communication network 12 communicates the biometric signal and the electromagnetic frequency to the medical professional. The medical professional analyzes the information received from the electronic device against a data base of healthy biometric signals and electromagnetic frequencies. Thus, the medical professional may identify health concerns associated with the user.

The medical professional creates a treatment regimen and the treatment regimen is communicated to the electronic device 14. Thus, the user may seek medical treatment without visiting a medical facility. Additionally, user may seek medical treatment while the user is in a remote location. The user may recommend a treatment regimen without the advice of the medical professional. The user may access data in the database to formulate a treatment regimen without medical intervention.

The treatment regimen may comprise a treatment signal of a recommended frequency to be communicated through the transmitter 30 and the transceiver 36. The user touches each of the depressions 24. Thus, the treatment signal is communicated to the user. The treatment signal may have a frequency correlating with Vega Test Frequencies or the like.

With respect to the above description then, it is to be realized that the optimum dimensional relationships for the parts of an embodiment enabled by the disclosure, to include variations in size, materials, shape, form, function and manner of operation, system and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A mobile health system comprising:
   a communication network;
   an electronic device being in electrical communication with said communication network, said electronic device having an input; and
   a sensing unit being removably coupled to said electronic device such that said sensing unit is in electrical communication with said electronic device, said sensing unit being configured to be touched by a user thereby facilitating said sensing unit to record a biometric signal generated by the user, said sensing unit being configured to communicate the biometric signal to said electronic device, said electronic device transmitting the biometric signal to the communication network wherein said communication network is configured to communicate the biometric signal to a medical professional thereby facilitating the medical professional to recommend a medical treatment corresponding to the biometric signal, said sensing unit further comprising a housing having a front surface, said front surface having a pair of depressions, said depressions being ovular and concave, each of said depressions being configured to be touched by the user, each of said depressions being comprised of an electrically conductive material wherein each of said depressions is configured to be in electrical communication with the user when the user touches said depressions; and
   a plug coupled to and extending from said housing, said plug being selectively couplable to said electronic device by insertion into said electronic device, said plug being a headphone jack.

2. The system according to claim 1, further comprising: a processor; and
   a biometric sensor being positioned within said housing, said biometric sensor being electrically coupled to said processor, said biometric sensor being electrically coupled to one of said depressions wherein said biometric sensor is configured to receive the biometric signal from the user.

3. The system according to claim 1, further comprising:
   a processor, said plug being electrically coupled to said processor; and
   a body wave sensor being positioned within said housing, said body wave sensor being electrically coupled to said processor, said body wave sensor being electrically coupled to one of said depressions wherein said body wave sensor is configured to receive am electromagnetic frequency from the user.

4. The system according to claim 1, further comprising:
   a processor; and
   said plug being electrically coupled to said processor, said plug being selectively electrically coupled to said input on said electronic device wherein said plug is configured to communicate the biometric signal and an electromagnetic frequency to said electronic device, said electronic device communicating the biometric signal and the electromagnetic frequency to said communication network wherein said communication network is configured to communicate the biometric signal and the electromagnetic frequency to the medical professional.

5. The system according to claim 1, further comprising:
   a processor; and
   a power supply being positioned within said housing, said power supply being electrically coupled to said processor, said power supply comprising at least one battery.

6. A mobile health system comprising:
   a communication network;
   an electronic device being in electrical communication with said communication network, said electronic device having an input; and
   a sensing unit being removably coupled to said electronic device such that said sensing unit is in electrical communication with said electronic device, said sensing unit being configured to be touched by a user thereby facilitating said sensing unit to record a biometric signal generated by the user, said sensing unit being configured to communicate the biometric signal to said electronic device, said electronic device transmitting the biometric signal to the communication network wherein said communication network is configured to communicate the biometric signal to a medical professional thereby facilitating the medical professional to recommend a medical treatment corresponding to the biometric signal, said sensing unit further comprising:
- a housing having a front surface, said front surface having a pair of depressions, each of said depressions being configured to be touched by the user, each of said depressions being comprised of an electrically conductive material wherein each of said depressions is configured to be in electrical communication with the user when the user touches said depressions;
- a processor being positioned within said housing;
- a biometric sensor being positioned within said housing, said biometric sensor being electrically coupled to said processor, said biometric sensor being electrically coupled to one of said depressions wherein said biometric sensor is configured to receive the biometric signal from the user;
- a body wave sensor being positioned within said housing, said body wave sensor being electrically coupled to said processor, said body wave sensor being electrically coupled to one of said depressions wherein said body wave sensor is configured to receive an electromagnetic frequency from the user;
- a plug being coupled to said housing, said plug being electrically coupled to said processor, said plug being selectively electrically coupled to said input on said electronic device wherein said plug is configured to communicate the biometric signal and the electromagnetic frequency to said electronic device, said electronic device communicating the biometric signal and the electromagnetic frequency to said communication network wherein said communication network is configured to communicate the biometric signal and the electromagnetic frequency to the medical professional; and
- a power supply being positioned within said housing, said power supply being electrically coupled to said processor, said power supply comprising at least one battery.

* * * * *